US00PP18332P2

(12) United States Plant Patent
Danziger

(10) Patent No.: US PP18,332 P2
(45) Date of Patent: Dec. 18, 2007

(54) ***TORENIA* PLANT NAMED 'DANMOON17'**

(50) Latin Name: ***Torenia* sp.**
Varietal Denomination: DANMOON17

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/488,600

(22) Filed: Jul. 19, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Foley & Lardner, LLP

(57) ABSTRACT

A new and distinct *Torenia* plant named 'DANMOON17' particularly characterized by plenty of delicate, funnel form, cup-shaped flowers with petals in shades of red-purple with a yellow blotch on lower petal; mounded bush, which maintains a compact, rounded plant habit; vigorous growth habit; densely branched plant, gracefully cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.
Variety denomination: 'DANMOON17'.

BACKGROUND OF THE INVENTION

The present invention relates to a new and distinct cultivar of *Torenia* plant, botanically known as *Torenia* sp. of the Scrophulariaceae family, and hereinafter referred to by the cultivar name 'DANMOON17'.

The new *Torenia* cultivar is a product of a controlled breeding program conducted by the inventor, Gabriel Danziger, in Moshav Mishmar Hashiva, Israel. The objective of the breeding program was to develop a new *Torenia* cultivar with red-purple flowers.

The new *Torenia* cultivar originated from an induced mutation by gamma rays of the *Torenia* cultivar designated 'TR-3-1202' (unpatented). The new *Torenia* cultivar was discovered and selected by the inventor, Gabriel Danziger, as a single flowering plant within the progeny of the stated mutation in a controlled environment in January of 2005 in Moshav Mishmar Hashiva, Israel.

Asexual reproduction of the new *Torenia* cultivar by soft tip cuttings was first performed in June of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANMOON17' which in combination distinguish this *Torenia* as a new and distinct cultivar:

1. Plenty of delicate, funnel form, cup-shaped flowers with petals in shades of red-purple with a yellow blotch on lower petal;
2. Mounded bush, which maintains a compact, rounded plant habit;
3. Vigorous growth habit;
3. Densely branched plant, gracefully cascading from hanging baskets;
4. Early flowering response and stays in full bloom in moderate climate;
5. Suitable as an annual for hanging pots outdoors under partial shade; and
6. Good weather tolerance with a preferred temperature range of 15° C. to 25° C.

Plants of the new *Torenia* cultivar 'DANMOON17' differ from the parental cultivar, 'TR-3-1202' in the following characteristics described in Table 1.

TABLE 1

| Characteristic | New Cultivar 'DANMOON17' | Parent 'TR-3-1202' (unpatented) |
|---|---|---|
| Mature Flower color | Petal shades of red-purple, with yellow blotch on lower petal | Petal shades of violet, with a yellow blotch on lower petal |
| Flower size | Depth: About 3.0 cm<br>Width: About 3.1 cm | Depth: About 3 cm<br>Width: About 3.0 cm |
| Growth habit | Cascading Bush | Cascading Bush |
| Flowering Time | 3 weeks from planting | 3 weeks from planting |

Of the many commercial cultivars known to the present inventor, the most similar in comparison to the new *Torenia* cultivar 'DANMOON17' is the *Torenia* cultivar 'ROSE MOON' (unpatented) in the following characteristics described in Table 2:

TABLE 2

| Characteristic | New Cultivar 'DANMOON17' | Comparison Cultivar 'ROSE MOON' (unpatented) |
|---|---|---|
| Mature Flower Color | Petal shades of red-purple, with yellow blotch on lower petal | Petal shades of light red-purple, with a yellow blotch on lower petal |
| Flower size | Depth: About 3.0 cm<br>Width: About 3.1 cm | Depth: About 3.5 cm<br>Width: About 3.8 cm |
| Growth habit | Cascading Bush | Cascading Bush |
| Flowering time | 3 weeks from planting | 10 weeks from planting |

BRIEF DESCRIPTION OF THE PHOTOGRAPHS

The accompanying photographs illustrate the overall appearance of the new *Torenia* cultivar 'DANMOON17' showing the colors as true as is reasonably possible with colored reproductions of this type. Colors in the photographs may differ slightly from the color values cited in the detailed botanical description, which accurately describe the color of 'DANMOON17'.

DETAILED BOTANICAL DESCRIPTION

Figure 1:
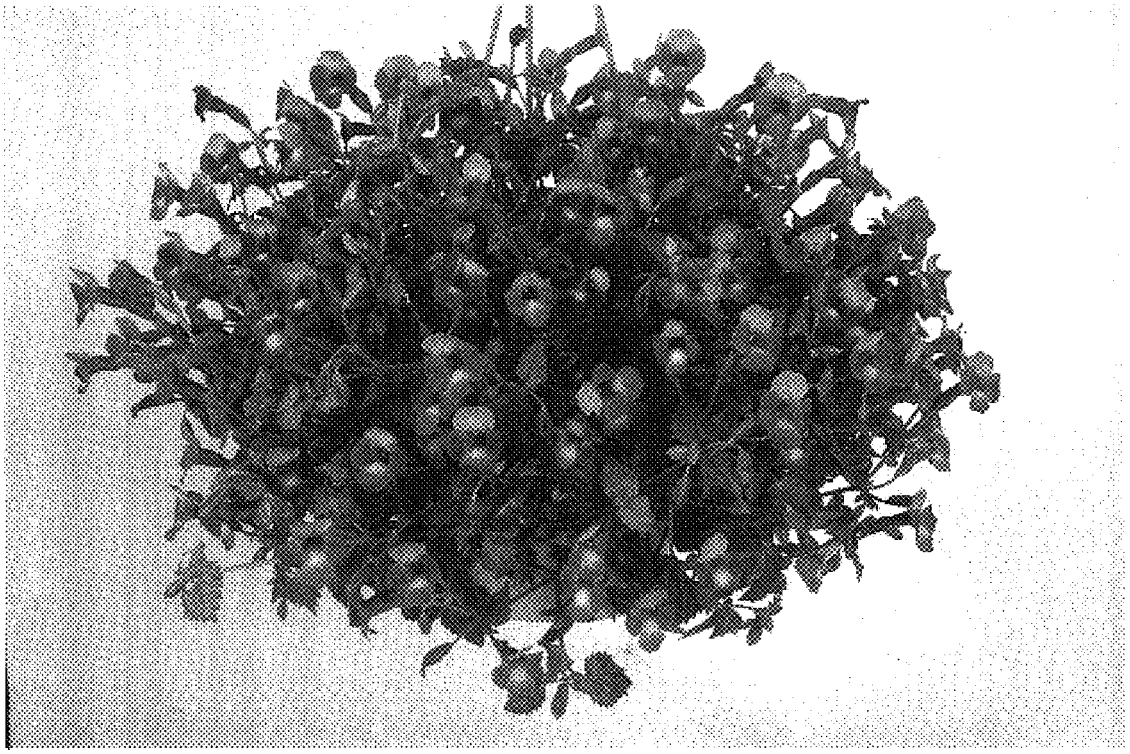
FIG. 1 shows a side perspective view of a typical flowering plant of 'DANMOON17' in a hanging planter at 3 months of age.
Figure 2:
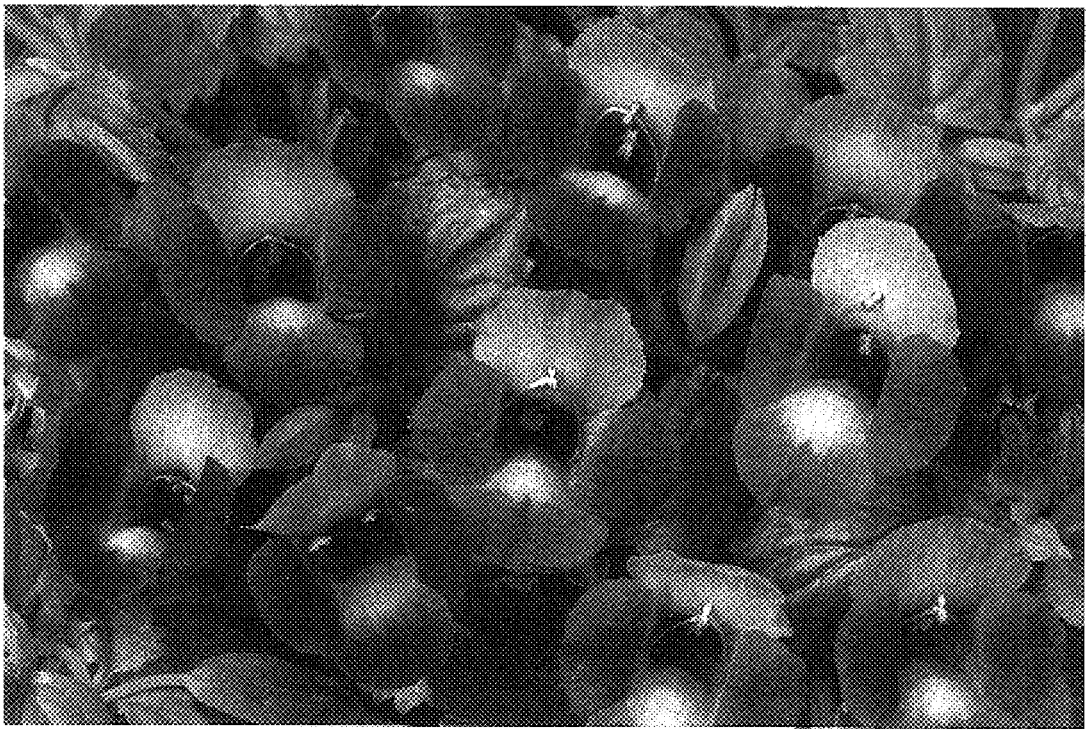
FIG. 2 shows a close-up of the typical flowers, buds and leaves of 'DANMOON17' at 3 months of age.

The new *Torenia* cultivar 'DANMOON17' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANMOON17' as grown in a greenhouse in Moshav Mishmar Hashiva, Israel, under conditions which closely approximate those generally used in commercial practice. Optimal growth conditions include that plants of 'DANMOON17' are grown outdoors in a moderate climate and indoors during the winter season. Irrigation and fertilization are recommended on a regular basis. Plants of 'DANMOON17' are usually grown in full sunlight, but partial shade is required in mid summer. Plants of 'DANMOON17' are fully-grown in 3 months from planting a cutting in the summer season and bloom all year-round in a moderate climate. Plants of 'DANMOON17' described herein were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'DANMOON17' were fertilized up to a level of 59 ppm N, 35.4 ppm P and 94.4 ppm K.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANMOON17' plants described is 12 weeks.

Parentage: *Torenia* cultivar designated 'TR-3-1202' (unpatented).

Propagation: Tissue culture and soft tip cuttings.

Plant:

*Form.*—Bush, cascading.

*Growth habit.*—Compact, rounded.

*Height.*—About 18 cm.

*Spread.*—About 50 cm.

*Cold tolerance.*—Frost tender. Temperatures below 8° C. may damage plants.

*Vigor.*—Vigorous growth; plants are fully-grown in 3 months from planting cuttings during summer season.

Stem:

*Color.*—RHS 146A, yellow-green.

*Length.*—About 25 cm.

*Diameter.*—About 3 mm.

*Pubescence.*—Minimal.

*Branching.*—About 15 to 30 main branches grow from the base and split into hundreds of secondary and tertiary branches.

*Length of internodes.*—1.5 cm to 8.5 cm.

Foliage:

*Overall shape.*—Deltoid.

*Apex.*—Acute.

*Base.*—Cordate.

*Size of leaf.*—Width: 2.5 cm to 3.7 cm. Length: About 4.5 cm.

*Margin.*—Serrate.

*Color.*—Center color of leaf: RHS 137A, green. Upper side: RHS 137A, green. Under side: RHS 146B, green.

*Leaf texture.*—Glabrous with sensible veins.

*Venation.*—Pattern: Anastomotic. Color: Upper surface: RHS 137A, green. Lower surface: RHS 146B, yellow-green.

*Petioles.*—Length: About 0.5 cm to 1.4 cm. Diameter: About 2 mm. Color: RHS 143A, green.

Flowers:

*Blooming period.*—All year round in a moderate climate or in a greenhouse environment. In Israel, flowering occurs between February and November outdoors.

*Flowering response time.*—About 3 weeks from planting.

*Flowering stem.*—Flowers appear along the growing stems.

*Quantity of flowers.*—Per stem: About 4 to 7; Per plant: About 200 to 350.

*Flowering longevity.*—On the plant: about 2 to 5 days, depending on temperature.

*Type.*—Single.

*Shape.*—Overall: funnel form; 5-winged; Corolla tube: cylindrical or often broadened above; Corolla: 2-lipped, the upper lip faintly 2-lobed, the lower lip 3-lobed.

*Orientation at opening.*—Slanted upward.

*Fragrance.*—None.

*Flower size.*—Depth: About 3.0 cm. Width: About 3.1 cm.

*Bud.*—Shape: Oblong, cylindrical, ellipsoid, 5-winged. Size: Length: About 1.7 mm. Diameter: About 0.9 mm. Color: Apex: RHS 146A, yellow-green. Base: RHS 146A, yellow-green.

*Texture.*—Pubescence on winged edges.

*Floral tube.*—Length: About 3.0 cm. Width: About 0.3 cm to 1.2 cm. Color: Outside: RHS 71A, red-purple (upper side) and RHS 65A, red-purple (lower side).

Inside: RHS 72A, red-purple (apex) and RHS 72C, red-purple (base).

*Petals.*—Number: Four, fused. Length: Upper Petal: About 2.5 cm; Side Petals: About 2.0 cm; Lower Petal: About 2.0 cm; Width: Upper Petal: About 2.6 cm; Side Petals: About 1.2 cm; Lower Petal: About 1.8 cm; Shape: Upper Petal: Overall: spatulate, Apex: rounded, Base: fused; Side Petals: Overall: spatulate, Apex: rounded, Base: fused; Lower: Overall: spatulate, Apex: rounded, Base: fused. Margin: Undulated and toothed. Color: Mature Petals: Upper Surface: Upper Petal: Near apex, RHS 10C, yellow, and near base, RHS 71C, red-purple, and margin, RHS 72B, red-purple; Side Petals: Entire petal, including margin, RHS 71A, red-purple; Lower Petal: Primarily RHS 71A, red-purple, with RHS 10A, yellow, blotch in the middle near base, and RHS 71A, red-purple color surrounding blotch and near base, and margin, RHS 71A, red-purple; Lower Surface: Upper Petal: Near apex, a mixture between RHS 10A, yellow, and RHS 71A, red-purple, and margin near base RHS 71A, red-purple. Side Petals: Near apex, RHS 70B, red-purple, and near base, RHS 8A, yellow, and margin, RHS 8A, yellow; Lower Petal: Near apex, a mixture between RHS 10A, yellow, and RHS 71A, red-purple, and near base RHS 10C, yellow, and margin, a mixture between RHS 10A, yellow, and RHS 71A, red-purple. Throat: Upper throat: RHS 82A, purple-violet; Lower throat: RHS 72C, red-purple. Immature Petals: Upper Surface: Upper Petal: Near apex, RHS 71B, red-purple, near base, RHS 71B, red-purple, and 12C, yellow, and margin, RHS 71B, red-purple. Side Petals: Near apex, RHS 61A, red-purple, near base, RHS 77B, purple, and margin RHS 61A, red-purple; Lower Petal: Primarily RHS 61A, red-purple, lower margin RHS N176A, greyed-orange, near apex RHS 162A, greyed-yellow; Lower Surface: Upper Petal: Near apex, RHS 64A, red-purple, and near base, RHS 71A, red-purple, and margin, RHS 64A, red-purple; Side Petals: Near apex, RHS 71A, red-purple, and near base, RHS 71A, red-purple, and margin, RHS 71A, red-purple; Lower Petal: Near apex, RHS 64A, red-purple, and near base, RHS 10C, yellow, and margin, RHS 64A, red-purple; Throat: Center of Flower: RHS 72B, red-purple.

*Sepals.*—Number: 5. Length: About 1.9 cm. Width: About 0.3 cm. Shape: Two-lobed, 5-winged. Apex: Acute. Base: Wedge shaped. Margin: Undulated. Color: RHS 146A, yellow-green.

*Peduncle.*—Length: About 1.0 to 3.2 cm. Diameter: About 2.5 mm. Color: RHS 146A, yellow-green.

Reproductive organs:

*Androecium.*—Stamen: Number: 2 pairs per flower, fused. Color: RHS N80A, purple-violet, and RHS 155C, white. Anther: Length: About 0.4 cm; upper anther shorter — about 0.3 cm. Width: About 0.1 cm (separate, usually there are two fused). Color: RHS 155C, white. Spur: Present. Filament: Length: About 1.3 cm; lower filaments are shorter about 0.6 cm. Width: About 0.4 mm. Color: RHS N80A, purple-violet. Pollen: Amount: Sparse. Color: RHS N155A, white. Requirements for pollination: Young flowers, vital pollen, and receptive, open stigma.

*Gynoecium.*—Pistil: Number: One per flower. Length: About 2.7 cm. Stigma: Length: About 0.2 cm. Width: About 0.2 cm. Color: RHS 76A, purple. Style: Length: About 2.2 cm. Color: RHS 75A, purple. Ovary: Number: 1. Length: About 0.5 cm. Width: About 0.2 cm. Color: RHS 144A, yellow-green.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANMOON17', as illustrated and described herein.

* * * * *